United States Patent
Boese et al.

(10) Patent No.: US 7,599,466 B2
(45) Date of Patent: Oct. 6, 2009

(54) OPERATING METHOD FOR X-RAY EQUIPMENT

(75) Inventors: Jan Boese, Eckental (DE); Günter Lauritsch, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/400,833

(22) Filed: Apr. 7, 2006

(65) Prior Publication Data

US 2007/0030945 A1  Feb. 8, 2007

(30) Foreign Application Priority Data

Apr. 8, 2005  (DE) .................. 10 2005 016 472

(51) Int. Cl.
*A61B 6/00* (2006.01)
(52) U.S. Cl. .................. 378/8; 378/4; 378/15
(58) Field of Classification Search .............. 378/8, 378/95, 901

See application file for complete search history.

(56) References Cited

U.S. PATENT DOCUMENTS

| | | | | |
|---|---|---|---|---|
| 4,182,311 | A * | 1/1980 | Seppi et al. ............ | 600/428 |
| 4,547,892 | A * | 10/1985 | Richey et al. ........... | 378/8 |
| 4,641,328 | A * | 2/1987 | Fujise .................. | 378/8 |
| 4,670,892 | A * | 6/1987 | Abele et al. ............ | 378/4 |
| 4,994,965 | A * | 2/1991 | Crawford et al. ........ | 378/95 |
| 5,014,293 | A * | 5/1991 | Boyd et al. ............ | 378/197 |
| 5,832,051 | A * | 11/1998 | Lutz .................... | 378/8 |
| 6,154,516 | A * | 11/2000 | Heuscher et al. ........ | 378/15 |
| 6,188,744 | B1 * | 2/2001 | Shinohara et al. ....... | 378/8 |
| 6,353,653 | B1 * | 3/2002 | Edic .................... | 378/8 |

(Continued)

FOREIGN PATENT DOCUMENTS

DE  19946092 A1  3/2001

(Continued)

OTHER PUBLICATIONS

Christophe Blondel, Grégoire Malandain, Régis Vaillant, Nicholas Ayache, "4D deformation field of coronary arteries from monoplane rotational X-ray angiography", Computer Assisted Radiology and Surgery 2003 Proceedings, Jun. 2003, pp. 1073-1078, vol. 1256 of ICS, Elsevier Science B.V., London, United Kingdom.

(Continued)

*Primary Examiner*—Edward J Glick
*Assistant Examiner*—Alexander H Taningco (57) ABSTRACT

A control device pivots an X-ray arrangement repeatedly between two final angular positions about a pivot axis. Projections of an object arranged in the region of the pivot axis and moving iteratively are detected at a plurality of angular positions and supplied to the control device. The control device also receives a phase position referring to the object and assigns the phase position to each projection. A computer selects one or more projections whose phase position corresponds at least approximately to a reconstruction phase position. If the computer has selected one projection for an angular position, it determines this projection as a reconstruction projection. If the computer has selected a plurality of projections for an angular position, it detects the reconstruction projection using these projections. The computer then detects a three-dimensional reconstruction of the object based on the reconstruction projection.

18 Claims, 7 Drawing Sheets

U.S. PATENT DOCUMENTS

| | | | |
|---|---|---|---|
| 6,426,990 B1* | 7/2002 | Cesmeli | 378/8 |
| 6,434,215 B1* | 8/2002 | Cesmeli | 378/8 |
| 6,438,196 B1* | 8/2002 | Cesmeli | 378/8 |
| 6,504,894 B2* | 1/2003 | Pan et al. | 378/8 |
| 6,522,712 B1* | 2/2003 | Yavuz et al. | 378/4 |
| 6,529,575 B1* | 3/2003 | Hsieh | 378/4 |
| 6,556,697 B1* | 4/2003 | Bruder et al. | 382/131 |
| 6,721,386 B2* | 4/2004 | Bulkes et al. | 378/8 |
| 6,865,248 B1* | 3/2005 | Rasche et al. | 378/8 |
| 6,909,769 B2* | 6/2005 | Bruder et al. | 378/8 |
| 7,221,728 B2* | 5/2007 | Edic et al. | 378/8 |
| 2003/0007593 A1* | 1/2003 | Heuscher et al. | 378/4 |
| 2004/0131140 A1* | 7/2004 | Bruder et al. | 378/4 |
| 2005/0175141 A1* | 8/2005 | Bruder et al. | 378/8 |

OTHER PUBLICATIONS

O. Wink, R. Kemkers, S.J. Chen, and J.D. Carroll, "Coronary Intervention Planning Using Hybrid 3D Reconstruction", MICCAI I, 2002, pp. 604-611, Springer-Verlag, Berlin Heidelberg.

J.B. Antoine Maintz and Max A. Viergever, "A survey of medical image registration", Medical Image Analysis, 1998, pp. 1-36, vol. 2, No. 1, Oxford University Press.

George Wolberg, "Digital Image Warping", Wiley-IEEE Computer Society Pr, Jul. 27, 1990, pp. 187-260, 1st edition, Chapter 7, ISBN: 0818689447, IEEE Computer Society Press Monograph, Los Alamitos, California.

Rueckert et al., "Non-Rigid Registration Using Free-Form Deformations: Applications to Breast MR Images", IEEE Transactions on Medical Imaging, Aug. 1999 pp. 712-721, vol. 18, Issue 8.

* cited by examiner

OPERATING METHOD FOR X-RAY EQUIPMENT

CROSS REFERENCE TO RELATED APPLICATIONS

This application claims priority to the German Application No. 10 2005 016 472.2, filed Apr. 8, 2005 which is incorporated by reference herein in its entirety.

FIELD OF INVENTION

The present invention relates to an operating method for X-ray equipment,
- whereby a control device pivots an X-ray arrangement at a pivoting speed between a first and a second final angular position about a pivot axis,
- whereby the X-ray arrangement comprises an X-ray source and an X-ray detector which diametrically oppose one another relative to the pivot axis,
- whereby the control device controls the X-ray arrangement during the pivoting process, such that the X-ray detector detects projections of an object to be examined arranged in the region of the pivot axis and moving iteratively, at a plurality of angular positions at detection moments and supplies the control device,
- whereby the control device stores the projections supplied thereto and the corresponding angular positions,
- whereby the control device receives a phase signal corresponding to a phase position of the object to be examined and assigns information corresponding to the respective phased position of the object to be examined to each stored projection.

The present invention further relates to a data carrier with a computer program stored on the data carrier for a control device of X-ray equipment to carry out such an operating method. The present invention also relates to a control device for X-ray equipment with such a data carrier and corresponding X-ray equipment.

The present invention also relates to an operating method for a computer,
- whereby the computer receives a number of projections of an object to be examined moving iteratively,
- whereby the object to be examined has been arranged in the region of a pivot axis during the detection of the projections, about which an X-ray arrangement has been pivoted between a first and a second final angular position,
- whereby the X-ray arrangement comprises an X-ray source and an X-ray detector which diametrically opposed one another relative to the pivot axis,
- whereby the projections were detected by the X-ray detector at a plurality of angular positions,
- whereby the corresponding angular position and information corresponding to a phase position of the object to be examined are assigned to each received projection,
- whereby the computer selects those projections where the phase position of the object to be examined corresponds at least approximately to a reconstruction phase position,
- whereby, using the selected projections, the computer detects a three-dimensional reconstruction of the object to be examined.

The present invention finally relates to a further data carrier with a computer program stored on the data carrier for a computer to carry out such an operating method and the corresponding computer itself.

BACKGROUND OF INVENTION

Such operating methods and devices are generally known. They are used for example in computer tomography and also in so-called C-arm systems and the like. By means of the projections detected, a three-dimensional reconstruction of the object to be examined is generally carried out. The object to be examined is therefore frequently, if not always, the beating heart of a human being.

To detect the projections, the X-ray arrangement is generally pivoted about a pivot angle of more than 180°. The pivot angle is, for example, between 195° and 220°. When the three-dimensional reconstruction of the object to be examined is to be detected according to the Feldkamp algorithm which is generally known to persons skilled in the art, the minimum value of the pivot angle is 180°+β. In this connection, β is the detection angle of the X-ray detector.

SUMMARY OF INVENTION

In computer tomography (CT) equipment the X-ray arrangement is pivoted relatively rapidly. Thus it is possible to achieve, for example, pivoting speeds where the X-ray arrangement is pivoted by the required pivot angle for only 0.1 to 0.2 seconds. This rather short time of well under one second is short enough to take a sufficiently large number of recordings from a sufficiently large angular range during a single cardiac cycle, whereby the heart is in diastole, in which it moves only relatively little, during the entire recording time.

However, with angiography systems and C-arm equipment, the time required to sweep over the required pivot angle is well over one second. Typical pivoting times are between a few seconds (for example 3 to 5 seconds) and one minute or more. With these X-ray devices, the aforementioned operating methods are therefore generally only used for detecting projections of statistical structures. Examples of such statistical structures are the human brain and the vascular system of the brain.

In spite of the long recording times, attempts have already also been made to use the aforementioned operating methods with angiography systems and C-arm equipment to detect images of the heart. Various approaches for this are known.

It is, for example, known to use so-called symbolic reconstruction methods instead of a full reconstruction method. With such reconstruction methods, it is assumed that the macrostructure of the object to be examined and to be reconstructed is already known. Using the evaluated projections only a remainder correction is then carried out. A few projections (generally between two and eight projections) are sufficient for such a remainder correction. The drawback of this method is that already to some extent, i.e. even before the evaluation of the first projection, it is assumed that the macrostructure of the object to be reconstructed is known.

A further approach according to the scientific paper by Onno Wink, Richard Kemkers, S.-Y James Chen, John D Carroll: 'Coronary Intervention Planning Using Hybrid 3D Reconstruction', MICCAI (1) 2002, pages 604 to 611, consists in selecting those projections where the phase position of the object to be examined corresponds approximately to a reconstruction phase position and to reconstruct the object to be examined using these selected projections. The more accurately the reconstruction phase position is to be maintained, the fewer projections are available for selection, however. The angular ranges within which these selected projections have been detected are also correspondingly small. Above all, however, large angular gaps are present between these angular ranges. This results in a great reduction of the reconstruction accuracy and indeed both relative to the possible contrast and also relative to the local resolution of the three-dimensional reconstruction.

More specifically, it is even possible to select the phase window to be larger around the reconstruction phase position. This, however, results in projections being used which originate from phase positions of the heart which diverge more markedly from one another. The actual movement of the object to be examined within this phase window is thus disregarded. This leads to errors and artefacts during the reconstruction, which likewise impair both the contrast and the local resolution.

It has also be attempted—see the scientific paper by Ch. Blondel, G. Malandain, R. Vaillant and N. Ayache: '4D deformation field of coronary arteries from monoplane rotational X-ray angiography', which appeared in Computer Assisted Radiology and Surgery 2003 Proceedings, Volume 1256 of ICS, London, United Kingdom, June 2003, Elsevier, pages 1073 to 1078—to compensate for the movement of the object to be examined, known in broad outline, in the projections by corresponding modifications. Even this approach, however, exhibits weaknesses in practical use. Moreover, it can only be used for objects to be examined which are highly contrasted. Finally, for these methods long computing times and/or user interactions are frequently required.

An object of the present invention is to provide operating methods by means of which the aforementioned drawbacks can be avoided, although the time required to sweep over the pivot angle is greater than a resting phase of the object to be examined.

Insofar as it relates to the detection of projections, the object is achieved by an operating method for X-ray equipment, in which a control device pivots an X-ray arrangement repeatedly at a pivoting speed between a first and a second final angular position about a pivot axis, the X-ray arrangement comprises an X-ray source and an X-ray detector which diametrically oppose one another relative to the pivot axis, the control device controls the X-ray arrangement during the pivoting processes, such that the X-ray detector respectively detects projections of an object to be examined moving iteratively and arranged in the region of the pivot axis with a plurality of angular positions at recording times and supplies the control device, the control device which stores projections supplied thereto and the corresponding angular positions and the control device receives a corresponding phase signal with a phase position of the object to be examined and assigns information corresponding to the respective phase position of the object to be examined to each stored projection.

The object is also further achieved within the scope of recording the projections by a data carrier with a computer program stored on the data carrier for a control device of X-ray equipment, whereby the computer program serves to carry out such an operating method. For the recording of projections the object is also achieved by a control device for X-ray equipment which comprises such a data carrier. Finally, the object is further achieved, insofar as it relates to the recording of projections, by X-ray equipment with a control device and an X-ray arrangement, whereby the X-ray arrangement comprises an X-ray source and an X-ray detector, which diametrically oppose one another relative to a pivot axis and whereby the control device is configured and connected to act with the X-ray arrangement such that the X-ray equipment can be operated according to such an operating method.

Insofar as it refers to the evaluation of projections, the object is achieved by an operating method for a computer, whereby the computer receives a number of projections of an object to be examined moving iteratively, whereby the object to be examined has been arranged during the detection of the projections in the region of a pivot axis, about which an X-ray arrangement has been pivoted between a first and a second final angular position, whereby the X-ray arrangement comprises an X-ray source and an X-ray detector which diametrically opposed one another relative to the pivot axis, whereby the projections have been detected by the X-ray detector at a plurality of angular positions, whereby the corresponding angular position and information corresponding to a phase position of the object to be examined are assigned to each received projection, whereby the computer selects those projections, in which the phase position of the object to be examined corresponds at least approximately to a reconstruction phase position, whereby for each angular position in which it has selected at least one of the projections, the computer checks whether it has accurately selected one of the projections or whether it has selected a plurality of projections, whereby for each angular position in which it has accurately selected one of the projections, the computer detects this projection for this angular position as a reconstruction projection, whereby for each angular position in which it has selected a plurality of these projections, the computer detects a reconstruction projection using at least one of these projections for this angular position, whereby the computer detects a three-dimensional reconstruction of the object to be examined using the reconstruction projections.

The object is also achieved relative to the evaluation of the projections by a data carrier with a computer program for a computer stored on the data carrier, whereby the computer program serves to carry out such an operating method. Finally, the object is further achieved, insofar as it relates to the evaluation of the projections, by a computer with such a data carrier.

As regards the recording of projections, the pivoting processes can always run from the first to the second final angular position. Preferably, however, the pivoting processes run alternately from the first to the second final angular position and from the second to the first final angular position.

Generally, the control device detects the information corresponding to the phase position of the object to be examined using the moments when the object to be examined adopts a desired phase position, and the recording times.

The control device can control the individual pivoting processes independently of the phase position of the object to be examined. Preferably, however, before each pivoting process, the control device checks at which angular positions of the X-ray detector projections have been recorded and stored up to this time, during which the desired phase position was approximately adopted by the object to be examined, and manipulates the pivoting process such that at least one portion of the projections, during which the object to be examined approximately adopts the desired phase position, is recorded at angular positions of the X-ray detector, when no projections have been detected and stored up to this time, during which the object to be examined approximately adopted the desired phase position.

The manipulation can, for example, be carried out by the control device which starts the pivoting process at a correspondingly evaluated start time. Alternatively or additionally, the manipulation can also be carried out by the control device varying the pivoting speed during the pivoting process.

Preferably, during the individual pivoting processes, the control device again monitors whether an omission criterion is fulfilled and controls the X-ray source optionally at least only at reduced capacity. As a result, the X-ray load of the object to be examined can be minimized. The omission criterion can for example be fulfilled when the phase position of the object to be examined is within an omission range. Alternatively or additionally the omission criterion can also be fulfilled when, during the temporary angular position of the X-ray detector and the temporary phase position of the object to be examined, a projection of the object to be examined has already been recorded and stored. During evaluation of the projections it is possible that for at least one of the angular positions in which it has selected a plurality of projections, the computer detects one of these projections as a reconstruction projection. It is, however, also possible that the computer, for at least one of the angular positions, in which it has selected a plurality of projections, detects the reconstruction projection using at least two (generally precisely two) of these projections. Which of these two methods the computer uses can, in particular, depend on the phase positions of the projections selected for the respective angular position with regard to the reconstruction phase position.

When the computer detects the respective reconstruction projection using at least two selected projections, it is possible for the computer to detect the reconstruction projection by an interpolation carried out pixel by pixel. This method has the advantage that it can be carried out relatively simply and rapidly. Generally, however, it leads to improved results, when the computer detects elastic image warping between at least two of the projections which it uses to detect the reconstruction projection and detects the reconstruction projection using the elastic image warping and at least one of the projections used to detect the elastic image warping. For more accurate detection of the elastic image warping, it is also possible that the computer is previously subjected to a structure detection for detecting the projections used to detect the elastic image warping, for example carries out an edge detection.

BRIEF DESCRIPTION OF THE DRAWINGS

Further advantages and details are revealed from the following description of an embodiment in conjunction with the drawings, in which.

DETAILED DESCRIPTION OF INVENTION

Figure 1:
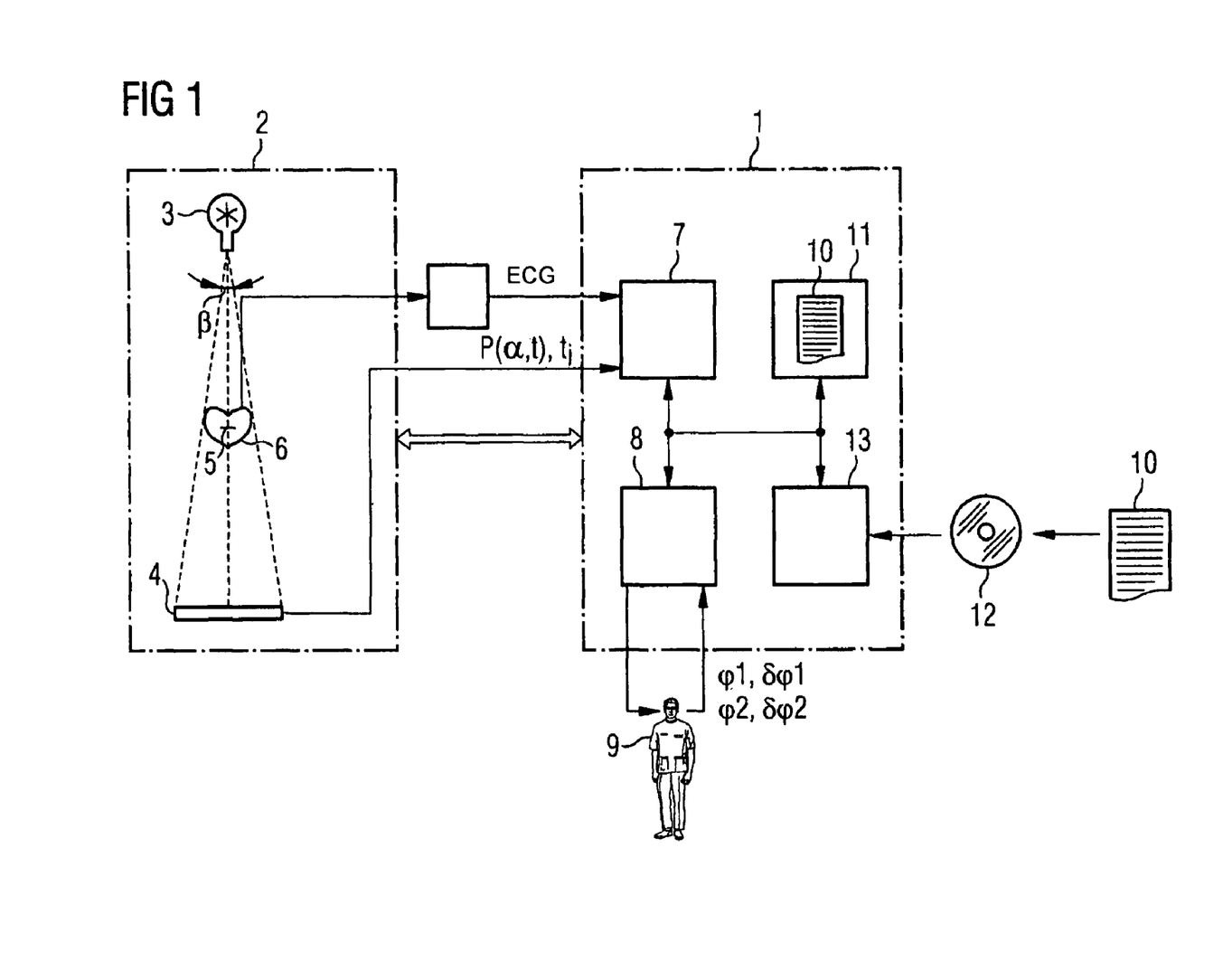
FIG. 1 is the main structure of X-ray equipment.

According to FIG. 1 X-ray equipment comprises a control device 1 and an X-ray arrangement 2. The X-ray arrangement 2 comprises, in turn, an X-ray source 3 and an X-ray detector 4. The X-ray source 3 and the X-ray detector 4 oppose one another diametrically relative to a pivot axis 5.

The control device 1 is, as is indicated in FIG. 1 by a double arrow, connected to act on the X-ray arrangement 2. It is therefore able to control the X-ray arrangement 2 and, in particular, to receive and to store projections P of an object to be examined 6 recorded by an X-ray detector 4. The object to be examined 6 is therefore generally arranged in the region of the pivot axis 5. The object to be examined 6 can, in particular, refer to an object to be examined 6 moving iteratively, for example, the beating heart 6 of a living person.

The control device 1 comprises, among other things, a computer unit 7 and a terminal 8 via which it can communicate with an operator 9. The mode of operation of the control device 1 is determined by a computer program 10 which is deposited in a program memory 11 of the control device 1, for example in a hard drive or in a non-volatile semi-conductor memory. The program memory 11 of the control device 1 thus corresponds to a data carrier 11 which is permanently assigned to the control device 1.

The computer program 10 can be supplied to the control device 1 in different ways. For example, it is possible that the computer program 10 of the control device 1 has been supplied via the Internet or another network device. In this case the computer program 10 is stored in a source on a data carrier and from which the computer program 10 is loaded into the control device 1. Both the network connection and the source and the data carrier located there are not shown in FIG. 1 for reasons of clarity. The computer program 10 can, however, be stored on a removable medium 12, for example a CD-ROM 12 or a USB memory stick, and is supplied to the control device 1 via a corresponding reading device 13.

Based on the programming with the computer program 10, the control device 1 (and thus also the X-ray equipment as a whole) carries out an operating method which will be described below in connection with FIGS. 2 to 6.

Figure 2:
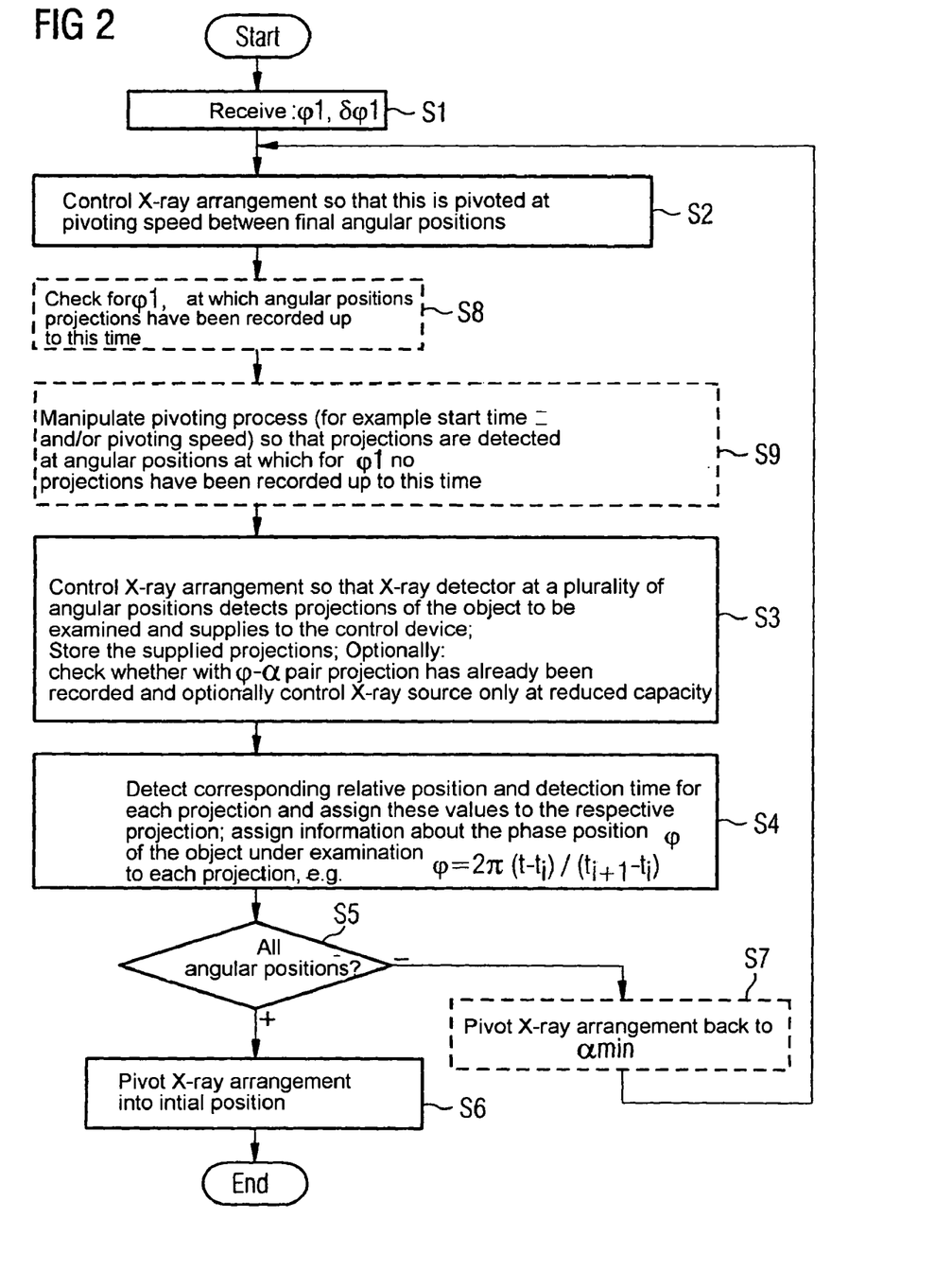
FIG. 2 is a flow diagram.

According to FIG. 2 the control device 1 is preset by the user 9 in a step S1, firstly a desired phase position $\phi1$ of the object to be examined 6 and a maximum allowable phase deviation $\delta\phi1$. The desired phase position $\phi1$ and the maximum allowable phase deviation $\delta\phi1$ are therefore generally determined such that the object to be examined 6 can be seen as unmoved within the phase window thus defined ($\phi1-\delta\phi1$ to $\phi1+\delta\phi1$) . The desired phase position $\phi1$ and the maximum allowable phase deviation $\delta\phi1$ are, for example, determined such that the heart 6 is in diastole, during which the heart 6 does not substantially move, in the entire phase window.

Moreover, the control device 1 controls the X-ray arrangement 2 in a step S2 so that the X-ray arrangement 2 is pivoted at a pivoting speed v from a first final angular position $\alpha$min to a second final angular position $\alpha$max about the pivot axis 5.

During the pivoting process the control device 1 controls the X-ray arrangement 2 in a step S3, such that the X-ray detector 4 at a plurality of angular positions $\alpha$ respectively records a projection P of the object to be examined 6 and supplies the control device 1. These projections P are stored by the control device 1—still within the scope of step S3.

The pivoting of the X-ray arrangement 2 is, as already mentioned, controlled by the control device 1. For every recorded projection P, the control device 1 therefore knows at which angular position $\alpha$ this projection P has been recorded. It is therefore able in a step S4 to assign the corresponding angular position $\alpha$ to each recorded projection P and to store this angular position $\alpha$ together with the projection P.

According to FIG. 2 the control device 1 also records at which recording times t it records the respective projections P. It also assigns the recording times t in the context of the step S4 to the corresponding projections P and stores them together with the projections P and the corresponding angular positions α.

Finally, according to FIGS. 1 and 2, the control device 1 receives a further ECG phase signal of the object to be examined 6, i.e. in the present case an ECG signal of the heart 6. The ECG phase signal corresponds to a phase position of the object to be examined 6. For example, the beginning of the systole of the heart 6 can be respectively identified using the so-called R-spike of the ECG signal.

Using the recording time t and the time $t_i$, at which—purely by way of example—the R-spikes of the ECG phase signal occur, a phase position φ of the object to be examined 6 can therefore be detected for each projection P. It is therefore possible that this detection is undertaken within the context of step S4 by the control device 1. It can, however, also be temporarily deferred. In this case the basic information itself, i.e. the recording times t and the times $t_i$ of the R-spikes, is information about the phase position φ of the object to be examined 6.

As already mentioned, the time during which the X-ray arrangement 2 is pivoted from the first final angular position αmin to the second final angular position αmax is so great that the object to be examined 6 during this pivoting process carries out numerous iterations of its motion cycle. In the present case, where the human heart 6 is under consideration, the heart 6 repeatedly beats. When the projections P are continuously recorded, the object to be examined 6 is therefore within the phase window which is determined by the desired phase position α1 and the corresponding maximum allowable phase deviation δφ1 only in the case of part of the projections P.

If it is known beforehand that a subsequent three-dimensional reconstruction of the object to be examined 6 is to take place only during the desired phase position φ1 (and/or within the maximum allowable deviation δφ1 about the desired phase position φ1), it is possible that the control device 1 controls the X-ray source 3 and the X-ray detector 4 only during a suitably selected time window after each ECG phase signal. Outside the time window an omission criterion is then fulfilled. The omission criterion consists, in this case, of the phase position φ of the object to be examined 6 being in an omission range during this time period.

As an alternative to a complete omission of these projections P the X-ray source 3 could simply be controlled at reduced capacity, for example so that it emits only a fraction (half, third, etc) of the normal X-ray radiation.

Figure 3:
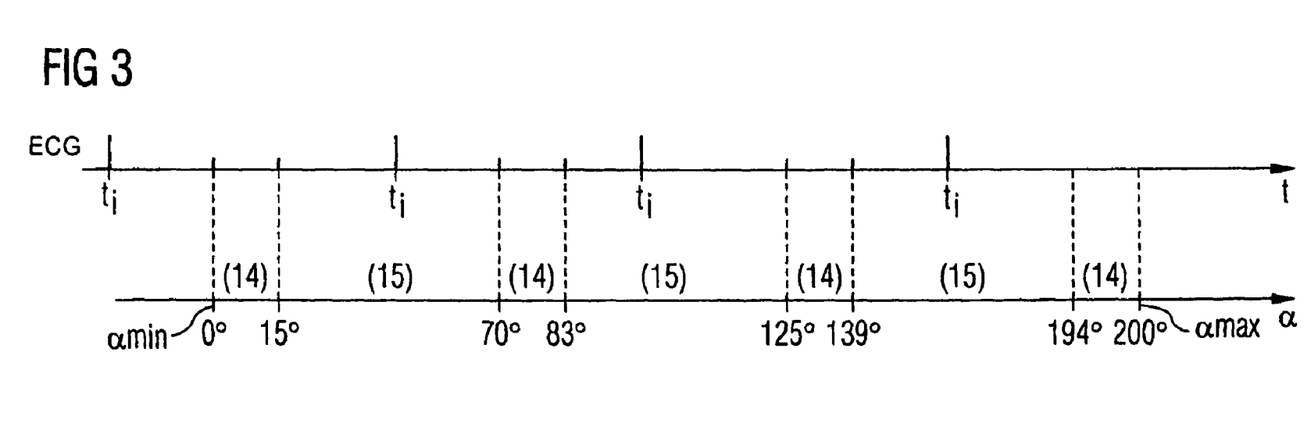
FIGS. 3 to 6 are timing diagrams and
FIGS. 7 to 9 are flow diagrams.

Independently therefrom, whether the X-ray source 3 is at times controlled at reduced capacity or at full capacity, the projections P, however, in which the phase position φ of the object to be examined 6 is in the desired phase window, sweep over only one part of the pivot angle. According to FIG. 3, they form angle windows 14 which are separated from one another by relatively large angular gaps 15. The angles given in FIG. 3 are therefore purely by way of example.

The method described above in connection with FIGS. 1 to 3, corresponds to the method of the prior art. With the projections P identified in the angle windows 14, a three-dimensional reconstruction of the object to be examined 6 is therefore already possible in principle. This three-dimensional reconstruction is, however, relatively unsatisfactory, both relative to the contrast and also relative to the local resolution. For this reason, the method previously disclosed is broadened according to the invention.

Thus, according to FIG. 2, the control device 1 firstly monitors in a step S5, whether—at least for the phase window predetermined in step S1—at all angular positions α between the final angular positions αmin and αmax, projections P of the object to be examined 6 have already been detected. If this is the case, the operating method for the X-ray arrangement 2 is substantially finished. Optionally, the X-ray equipment can still be pivoted into its initial position in a step S6.

At least according to the initial execution of steps S2 to S5, however, the aforementioned angle gaps 15 occur. The control device 1 therefore returns to step S2, and once more executes steps S2 to S5. Preferably, the control device 1 therefore returns directly to step S2. Thus the individual pivoting processes are then executed alternately from the first to the second final angular position αmin, αmax and from the second to the first final angular position αmax, αmin. This results, in particular, in a time-optimized operation of the X-ray equipment.

It could also be possible, however, to carry out a step S7 between steps S5 and S2, in which the X-ray arrangement 2 is pivoted back into the first final angular position αmin, without projections P of the object to be examined 6 being recorded. In this case, the pivoting processes always run from the first to the second final angular position αmin, αmax. Step S7 is, however, only optional and therefore in FIG. 2 only shown in dotted lines. However, irrespective of the presence of step S7 the control device 1, due to the multiple execution of steps S2 to S5, pivots the X-ray arrangement 2 repeatedly between the final angular positions αmin, αmax.

Carrying out steps S2 to S5 during a further cycle is, in principle, as already described above. As in contrast to the above description of the first cycle, during subsequent cycles through steps S2 to S5, angular positions α already exist in which projections P of the object to be examined 6 have already been recorded, the method of steps S2 to S5 is slightly modified. Thus steps S8 carried out between steps S2 and S3.

In step S8, the control device 1 checks the desired phase position φ1 (and/or for the phase window defined by the desired phase position φ1 and the maximum allowable phase deviation δφ1) at which angular positions α of the X-ray detector 4 projections P of the object to be examined 6 have been recorded and stored up to this time. In step S9, the control device 1 manipulates the respective pivoting process such that at least one part of the projections P, during which the object to be examined 6 adopts the desired phase position φ1 (and/or during which the phase position φ of the object to be examined 6 is in the phase window defined by the desired phase position φ1 and the maximum allowable phase deviation δφ1) is recorded at angular positions α of the X-ray detector 4, where no such projections P of the object to be examined 6 have been identified and stored up to this time. For example, based on an R-spike of the ECG signal, the control device 1 can correspondingly delay the pivoting process (and/or begin at a correspondingly detected starting point). Alternatively or additionally, it is also possible within the scope of step S9 that the control device 1 varies the pivoting speed v during the pivoting process. Optionally, this variation can, as such, even be optimized during pivoting.

More specifically, steps S8 advantageous, but not obligatory. For this reason they are shown in FIG. 2 only as dotted lines. When steps S8 and S9 are omitted, the control device 1 controls the individual pivoting processes independently of the phase position of the object to be examined 6.

It is furthermore possible according to FIG. 2 during the further cycles through steps S2 to S5 within the scope of step S3 to monitor continuously whether during the temporary angular position α of the X-ray detector 4 and the temporary phase position φ of the object to be examined 6 a projection P of the object to be examined 6 has already been recorded and stored. When this is the case, —similar to the procedure when the phase position φ of the object to be examined 6 is in the omission range—the X-ray source 3 can be controlled at reduced capacity, possibly even switched off completely.

Figure 4:
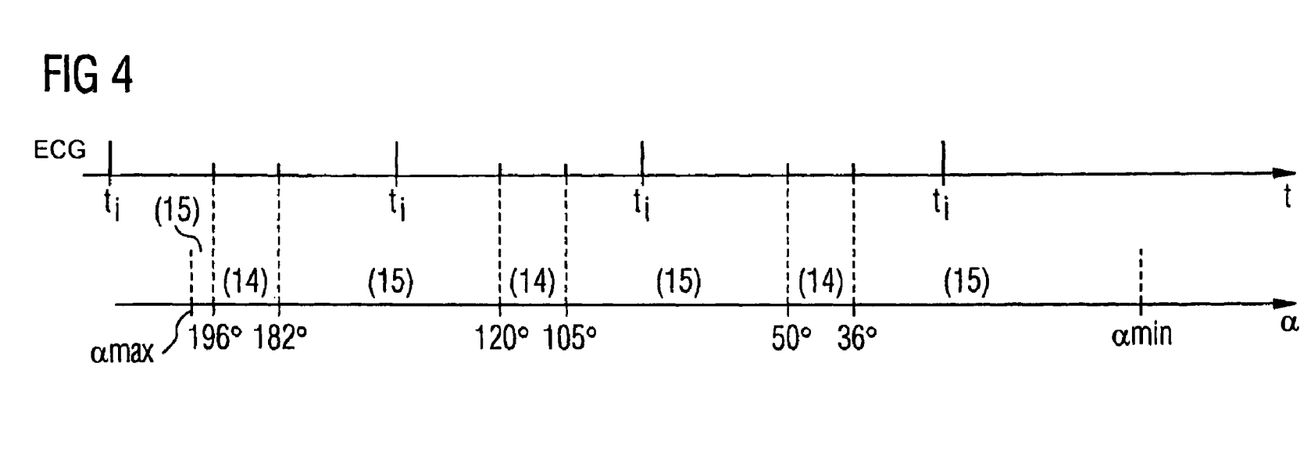
Figure 5:
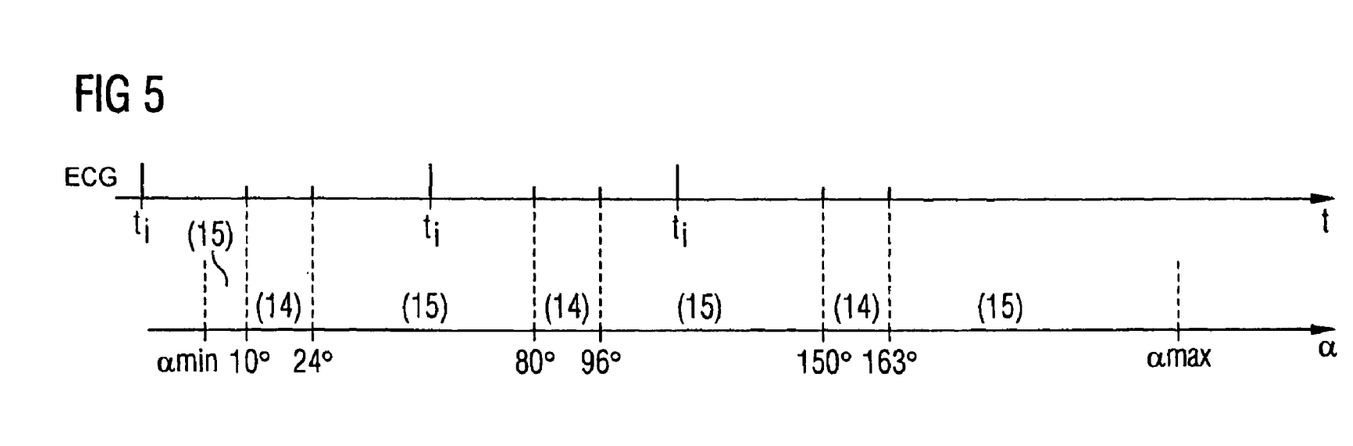
Figure 6:
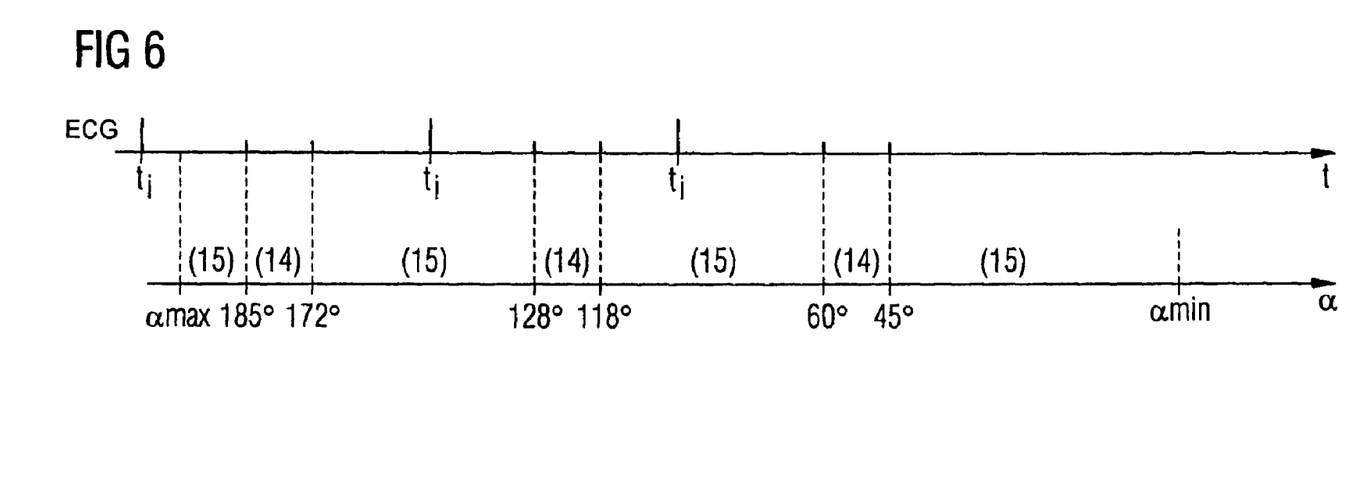

Based on the second execution of steps S2 to S5—this time optionally with steps S8 and S9—according to FIG. 4 a plurality of projections P are also detected, whereby—similar to FIG. 3—angle windows 14 are also formed, within which the projections P are recorded, during which the object to be examined 6 is in the predetermined phase window. The angles given in FIG. 4 are therefore—again similar to FIG. 3—purely by way of example. In FIG. 4, however, the angle windows 14 of FIG. 3 are systematically different from those of FIG. 4. More specifically, they can possibly overlap, but are not congruent. As a result, the effective angle windows 14 are thus widened and the effective angle gaps 15 reduced in size. The same applies to the third, the fourth and further cycles, whereby the third and fourth cycles through steps S2 to S5 are shown by way of example in FIGS. 5 and 6.

It is thereby achieved that a set of projections P is gradually recorded and stored, whereby the set of projections P contains at least one projection P for every angular position α of the X-ray detector 4, in which the phase position φ of the object to be examined 6 is within the predetermined phase window, i.e. at least approximately corresponds to the desired phase position φ1. As a result, it is possible, using this set of projections P, to detect a good three-dimensional reconstruction of the object to be examined 6.

Before more detail is given about the detection of the three-dimensional reconstruction of the object to be examined 6 below, it should be pointed out that the evaluation of the set of projections P described below is possible, namely in connection with the identification of the projections P. In principle, this evaluation is however separate from the recording of projections P. Whether it takes place by means of the control device 1 which is denoted hereinafter for this purpose as a computer 1, or by means of a separate evaluation computer is irrelevant within the context of the present invention. It is only of significance that the computer 1—for example within the context of the detection method of FIG. 2—receives the corresponding number of projections P of the object to be examined 6, that the object to be examined 6—see, for example, FIG. 1—has been arranged during the recording of the projections P in the region of the pivot axis 5, that the X-ray arrangement 2 comprises an X-ray source 3 and an X-ray detector 4 which were diametrically opposed to one another relative to the pivot axis 5, and has been pivoted between the final angular positions αmin, αmax and that the projections P are detected by the X-ray detector 4 at a plurality of angular positions a and the corresponding angular position α and information corresponding to the phase position φ of the object to be examined 6 are assigned to each received projection P.

Moreover, it is naturally required that the computer 1—for example by means of the computer program 10—is correspondingly programmed, so that it is able to carry out operating methods described in more detail below in connection with FIG. 7.

Figure 7:
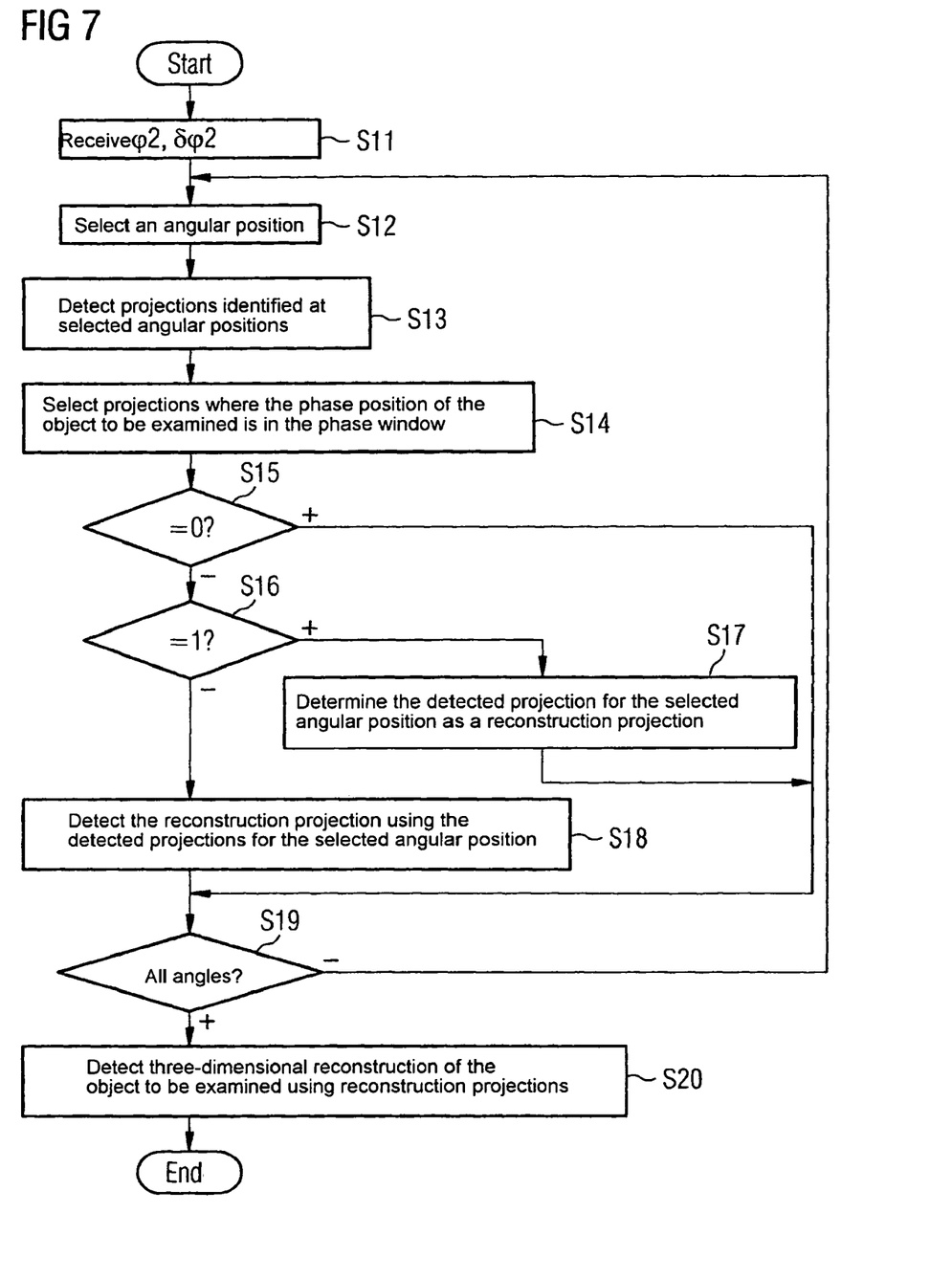

According to FIG. 7 in a step S11—similar to step S1 of FIG. 1—a reconstruction phase position φ2 and an associated maximum allowable phase deviation δφ2 are predetermined by the computer 1. The reconstruction phase position φ2 can therefore be identical to the desired phase position φ1. This is however not absolutely necessary, depending on the position of the particular case.

In a step S12 the computer 1 selects an angular position α. For this angular position α the computer detects in a step S13 the corresponding projection P, i.e. the projections P which have been recorded for this angular position α. In a step S14, the computer 1 selects from these projections P those projections P where the phase position φ of the object to be examined 6 is in the phase window which is defined by the reconstruction phase position φ2 and the corresponding maximum allowable phase deviation δφ2, in which the phase position is φ, i.e. between φ2-δφ2 and φ2+δφ2.

The number of projections P detected in step S14 can be zero. This is verified in step S15. In this case it is possible to proceed immediately to step S19.

The number of projections P detected in step S14 can, however, also be exactly equal to one, which is checked in step S16. When this occurs, the computer 1 establishes, in a step S17 for the currently selected angular position α, that this one projection P is a reconstruction projection P.

Otherwise, the computer 1 has been able to locate a plurality of projections P for the currently selected angular position α which are located around the reconstruction phase position φ2 within the allowable phase window. In this case, for the currently selected angular position α and using at least one of these projections P for this angular position α, the computer 1 detects a reconstruction projection P in a step S18.

Both from step S15 (already mentioned) and from steps S17 and S18 the computer 1 continues to carry out the method with step S19. In step S19, the computer 1 checks whether steps S12 to S18 have already been carried out for all angular positions α. When this is not the case, the computer 1 returns to step S12 where it selects a further angular position α which has not been checked until now. Otherwise the determination and/or detection of the reconstruction projections P is terminated. In this case the computer 1 continues the operating method of FIG. 7 according to the invention with a step S20. In step S20 the computer 1 detects, using the reconstruction projections P, a three–dimensional reconstruction of the object to be examined 6. Typically, this takes place according to the Feldkamp algorithm generally known to the person skilled in the art.

Various methods are possible for the implementation of step S18 of FIG. 7.

Figure 8:
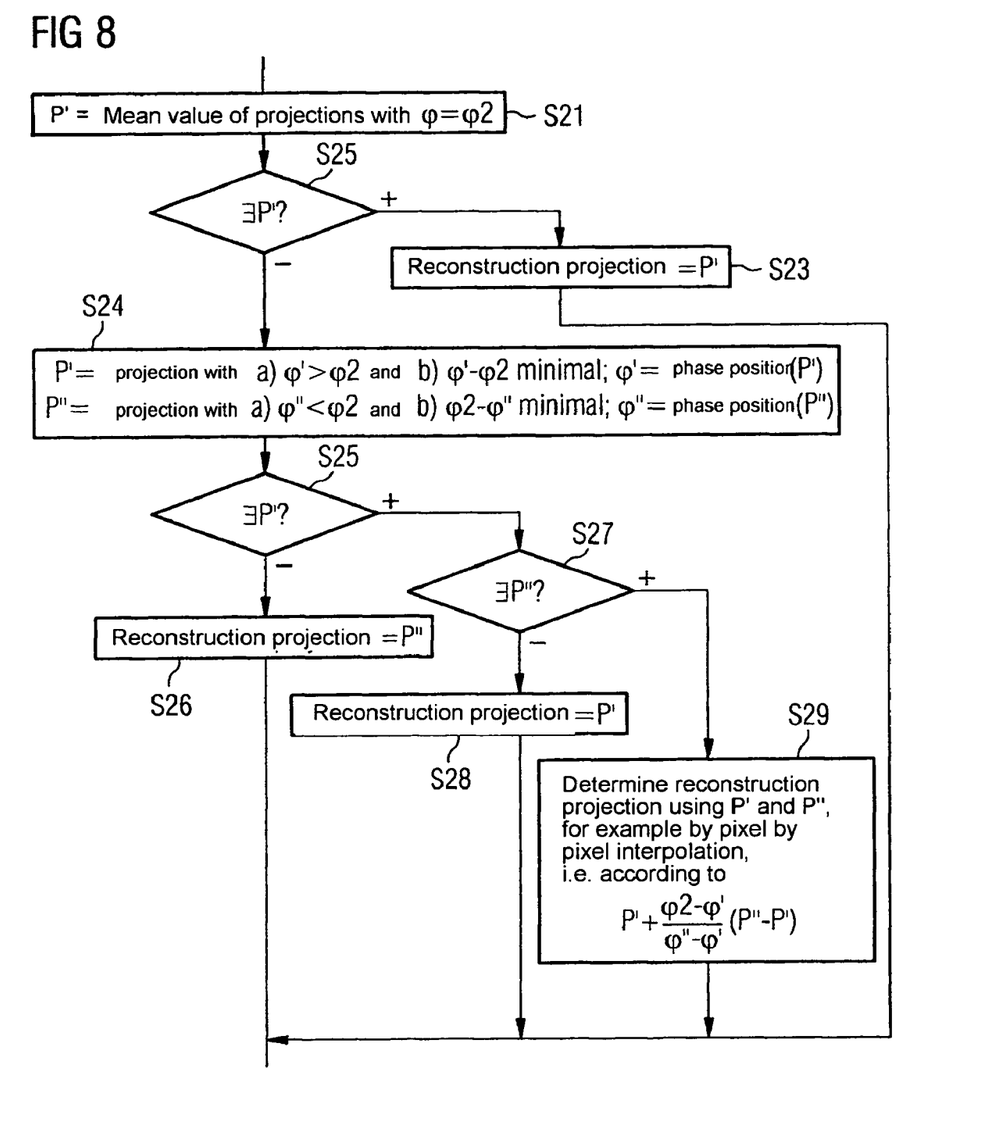

It is therefore possible according to FIG. 8, for example, to check firstly in steps S21 and S22, whether at the currently selected detection angle α at least one projection P exists whose phase position φ exactly coincides with the reconstruction phase position φ2. When this is the case, the average of these projections P is determined in a step S23 for this angular position α as a reconstruction projection P.

If, however, no such projection P is detected, in a step S24 an attempt is made for the currently selected angular position α to detect a first and a second auxiliary projection P', P'''. The auxiliary projections P', P''' must naturally have been detected at the currently selected angular position α. Phase positions φ', φ''' which bracket the reconstruction phase position φ2 are assigned thereto.

In a step S25 the computer checks whether it has been able to find the first auxiliary projection P'. If this is not the case, it determines in a step S26 the second auxiliary projection P''' for the reconstruction projection P for the currently selected angular position α.

If, however, it has been able to find the first auxiliary projection P', the computer checks, in a step S27, whether it has been able to find the second auxiliary projection P'''. If this is not the case, the computer 1 determines in a step S28 the first auxiliary projection P' for the currently selected angular position α for the reconstruction projection P.

If the computer 1 has been able to find both the first auxiliary projection P' and the second auxiliary projection P''', in a step S29 using the two auxiliary projections P', P''' for the currently selected angular position α the computer 1 detects the corresponding reconstruction projection P.

A plurality of methods are provided to implement step S29. The simplest is, as shown in FIG. 8, when the computer 1 detects the corresponding reconstruction projection P by a simple interpolation carried out pixel by pixel. Alternatively, however, step S29 can also be implemented as described below in connection with FIG. 9.

Figure 9:
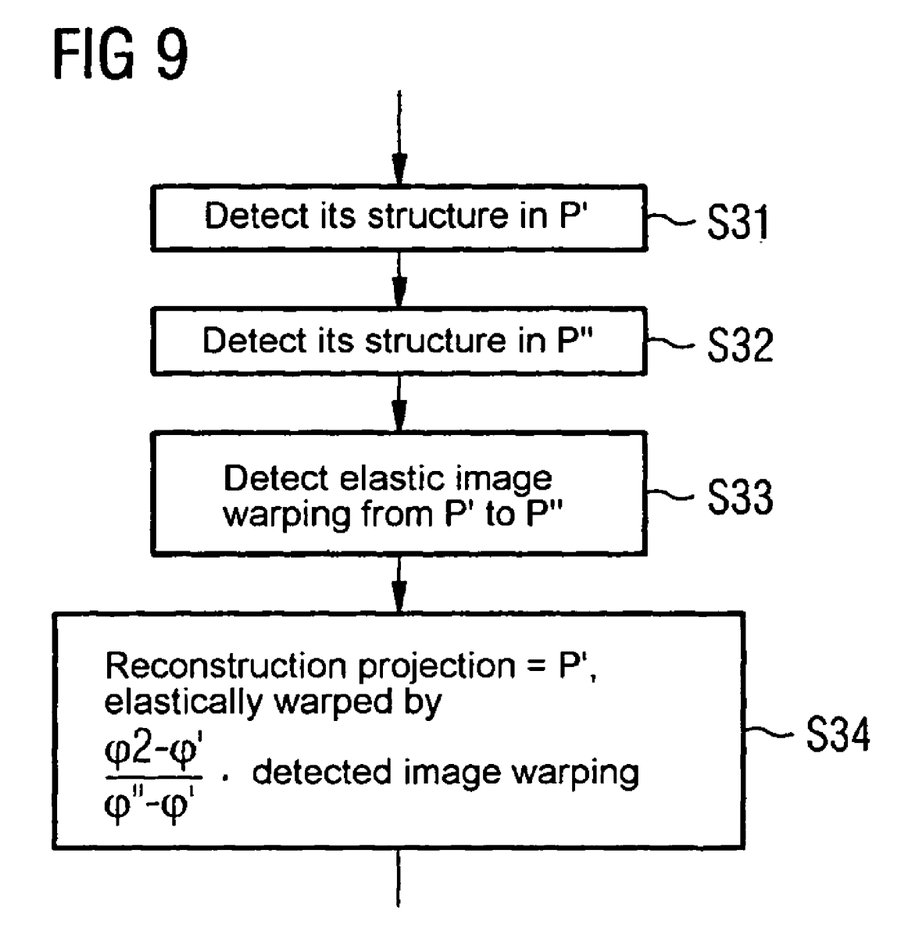

According to FIG. 9, the computer 1 subjects the first auxiliary projection P' to a structure detection in a step S31. A typical example of such a structure detection is an edge detection which is generally known to persons skilled in the art.

In a step S32 the computer 1 also subjects the second auxiliary projection P''' to a structure detection. Steps S31 and S32 are therefore only optional as although they improve the quality of a subsequent step S33, step S33 can be carried out without steps S31 and S32.

In step S33 the computer 1 detects elastic image warping between the auxiliary projections P', P'''. Methods for detecting the elastic image warping are generally known to persons skilled in the art and, for example, described in detail in J. B. A. Maintz, M. A. Viergever: 'A survey of medical image registration', Medical Image Analysis 2 (1) (1998), 1-36 or D. Rueckert, L. I. Sonoda, C. Hayes: 'Non-rigid registration using free-form deformations: Applications to breast MR images', IEEE Trans. on Medical Imaging 18 (8) (1999), 712-721.

Moreover, in a step S34 using the elastic image warping detected in step S33 and at least one of the auxiliary projections P', P''' the computer 1 detects the reconstruction projection (P). Such methods are known to persons skilled in the art by the terms 'image morphing'and 'image warping' and for example described in George Wolberg: 'Digital Image Warping' (IEEE Computer Society Press Monograph), Wiley-IEEE Computer Society Pr; 1st edition (Jul. 27, 1990), ISBN: 0818689447, chapter 7,pages 187 to 260.

By means of the method according to the invention, high-quality three-dimensional reconstructions of the object to be examined 6 can therefore be detected, although the object to be examined 6 moves iteratively and the time for pivoting the X-ray arrangement 2 is greater than the cycle time of the object to be examined 6.

The invention claimed is:

1. A method of operating X-ray equipment, comprising:
repeatedly pivoting an X-ray arrangement about a pivot axis at a pivoting speed between a first and a second final angular position, by a control device, the X-ray arrangement comprising an X-ray source and an X-ray detector diametrically opposed to each other relative to the pivot axis;
providing a phase signal representing a phasing of an examination object to the control device;
controlling the X-ray arrangement during the pivoting such that the X-ray detector only acquires projections of an iteratively moving examination object during selected time windows in time periods based on the phase signal at a plurality of acquisition points in time and at a plurality of angular positions of the X-ray detector, the examination object arranged in a range of the pivot axis;
transmitting the acquired projections to the control device by the X-ray detector;
storing the transmitted projections and the respective angular positions, by the control device;
assigning to each stored projection a phase information element related to the phasing of the examination object, by the control device;
selecting a phase position, and a maximum allowable deviation therefrom, relative to the phase signal for three dimensional reconstruction of the object;
selecting from the projections those projections having phase positions within the maximum allowable deviation from the selected phase position;
determining for each selected projection the respective angular position of the X-ray detector; and
calculating a three-dimensional reconstruction of the examination object from the selected projections and the determined respective angular positions for use in a medical examination.

2. The method according to claim 1, wherein the pivoting alternately extends from the first to the second final angular position and from the second to the first final angular position.

3. The method according to claim 1, wherein the control device determines the phase information elements based upon reference points in time and the acquisition points in time, the reference points in time corresponding to such points in time when the iteratively moving examination object has a reference phasing.

4. The method according to claim 3, further comprising:
determining by the control device before each pivoting of the X-ray arrangement such previous angular positions of the X-ray detector at which the X-ray arrangement has acquired projections of the examination object having the reference phasing; and
adjusting the pivoting of the X-ray arrangement by the control device such that:
at least part of the projections of the examination object are acquired at angular positions of the X-ray detector different from the previous angular positions; and the part of the projections of the examination object have the reference phasing.

5. The method according to claim 4, wherein adjusting the pivoting of the X-ray arrangement by the control device includes determining a starting time for the adjusted pivoting and executing the adjusted pivoting at the determined starting time.

6. The method according to claim 4, wherein adjusting the pivoting of the X-ray arrangement by the control device includes adjusting a pivoting speed and executing the adjusted pivoting at the adjusted pivoting speed.

7. The method according to claim 1, further comprising:
reducing capacity of the X-ray source to acquire projections during portions of the time periods other than the time windows.

8. The method according to claim 7, wherein reducing capacity suspends the acquisition of the projections.

9. The method according to claim 1, wherein the projections are continuously recoded by the X-ray detector during pivoting X-ray arrangement from the first final angular position to the second final angular position.

10. A software program embedded in a computer readable medium for operating an X-ray equipment, comprising software modules programmed and configured to:
repeatedly pivot an X-ray arrangement about a pivot axis at a pivoting speed between a first and a second final angular position, the X-ray arrangement comprising an X-ray source and an X-ray detector diametrically opposed to each other relative to the pivot axis;

provide a phase signal representing a phasing of an examination object to the control device;

control the X-ray arrangement during the pivoting such that the X-ray detector only acquires projections of an iteratively moving examination object during selected time windows in time periods based on a phase signal at a plurality of acquisition points in time and at a plurality of angular positions of the X-ray detector, the examination object arranged in a range of the pivot axis;

transmit the acquired projections to a control device of the X-ray equipment;

store the transmitted projections and the respective angular positions in the control device;

assign to each stored projection a phase information element related to the phasing of the examination object;

selecting a phase position, and a maximum allowable deviation therefrom, relative to the phase signal for three dimensional reconstruction of the object;

selecting from the projections those projections having phase positions within the maximum allowable deviation from the selected phase position;

determining for each selected projection the respective angular position of the X-ray detector; and calculating a three-dimensional reconstruction of the examination object from the selected projections and the determined respective angular positions for use in a medical examination.

11. A method of operating a computer for creating three dimensional medical images to be used in a medical examination, comprising:

feeding to the computer a plurality of projections of an examination object as the object undergoes cyclic motion, the projections recorded by an X-ray arrangement while pivoting the X-ray arrangement about a pivot axis between a first and a second final angular position, the X-ray arrangement comprising an X-ray source and an X-ray detector arranged diametrically opposed to each other relative to the pivot axis, the projections recorded at a plurality of angular positions of the X-ray detector, each projection including information elements about the respective angular position of the X-ray detector and about a phasing of the examination object;

providing a phase signal representing a phase in the motion cycle of the examination object;

selecting a phase position, and a maximum allowable deviation therefrom, relative to the phase signal for three dimensional reconstruction of the object;

selecting from the projections those projections having phase positions within the maximum allowable deviation from the selected phase position;

determining for each selected projection the respective angular position of the X-ray detector; and calculating a three-dimensional reconstruction of the examination object from the selected projections and the determined respective angular positions for use in the medical examination.

12. The method according to claim 11, further including, for calculating the three-dimensional reconstruction:

determining for each determined angular position of the X-ray detector if the respective angular position has either exactly one or a number of selected projections;

selecting for each angular position of the X-ray detector having exactly one selected projection the exactly one selected projection as a reconstruction projection of the respective angular position;

determining for each angular position of the X-ray detector having a number of selected projections a reconstruction projection of the respective angular position from the number of selected projections.

13. The method according to claim 11, wherein determining the reconstruction projection of the respective angular position from the number of selected projections includes selecting one of the number of selected projections as the reconstruction projection of the respective angular position.

14. The method according to claim 11, wherein determining the reconstruction projection of the respective angular position from the number of selected projections is based on at least two of the number of selected projections.

15. The method according to claim 14, wherein the reconstruction projection of the respective angular position is determined from the at least two selected projections using an interpolation algorithm, the interpolation algorithm calculation determining each pixel of the reconstruction projection from the respective pixels of the at least two selected projections.

16. The method according to claim 14, wherein the reconstruction projection of the respective angular position is determined from the at least two selected projections by:

calculating an elastic translational displacement from the at least two selected projections; and applying the calculated elastic translational displacement to one of the at least two selected projections.

17. The method according to claim 16, wherein a pattern recognition algorithm is applied to the at least two selected projections before calculating the elastic translational displacement, the pattern recognition algorithm configured to detect specific structures present in the at least two selected projections.

18. The method according to claim 17, wherein the specific structures include an edge.

* * * * *